United States Patent [19]

Harbour

[11] Patent Number: 5,431,285
[45] Date of Patent: Jul. 11, 1995

[54] VEHICLE UNLOADING FACILITY WITH COMPUTER DIRECTED SAMPLING

[75] Inventor: Earl E. Harbour, Proctorville, Ohio
[73] Assignee: Coal Systems Corporation, Proctorville, Ohio
[21] Appl. No.: 152,885
[22] Filed: Nov. 16, 1993

Related U.S. Application Data

[63] Continuation of Ser. No. 932,558, Aug. 20, 1992, abandoned, which is a continuation-in-part of Ser. No. 588,829, Sep. 27, 1990, abandoned.

[51] Int. Cl.$^6$ ................................................ B03B 9/00
[52] U.S. Cl. ............................................ 209/2; 209/3; 241/DIG. 38; 414/21
[58] Field of Search ................ 414/376, 572, 574, 387, 414/389, 584, 401, 201, 786, 21; 241/DIG. 38; 209/3, 656, 657, 2

[56] References Cited

U.S. PATENT DOCUMENTS

| | | |
|---|---|---|
| 396,197 | 1/1889 | Dodge . |
| 2,251,990 | 8/1941 | Young . |
| 3,606,050 | 9/1971 | Silver . |
| 3,660,038 | 5/1972 | Brewer .................... 241/DIG. 38 X |
| 3,802,584 | 4/1974 | Sackett, Sr. et al. . |
| 3,922,975 | 12/1975 | Reese ........................ 241/DIG. 38 X |
| 4,077,847 | 3/1978 | Choi et al. ............... 241/DIG. 38 X |
| 4,098,464 | 7/1978 | Niedner et al. ......... 241/DIG. 38 X |
| 4,231,478 | 11/1980 | Stone ................... 209/657 X |
| 4,314,241 | 2/1982 | La Plante et al. . |
| 4,326,425 | 4/1982 | Gundersen et al. . |
| 4,358,238 | 9/1982 | Ely . |
| 4,359,639 | 11/1982 | Wykes et al. . |
| 4,370,201 | 1/1983 | Lowenhaupt . |
| 4,486,894 | 12/1984 | Page et al. . |
| 4,531,093 | 1/1985 | Rollwitz et al. . |
| 4,548,087 | 10/1985 | Huck . |
| 4,558,602 | 12/1985 | Redding . |
| 4,562,044 | 12/1985 | Bohl . |
| 4,582,992 | 4/1986 | Atwell et al. . |
| 4,591,718 | 5/1986 | Amer . |
| 4,631,125 | 12/1986 | Parks . |
| 4,669,674 | 1/1987 | Oldengott et al. . |
| 4,799,799 | 1/1989 | Sapko et al. . |
| 4,813,839 | 3/1989 | Compton . |
| 4,841,153 | 6/1989 | Wormald . |
| 4,882,927 | 11/1989 | Gould . |
| 4,916,719 | 4/1990 | Kawatra et al. . |
| 4,988,044 | 1/1991 | Weitzman et al. ..... 241/DIG. 38 X |

FOREIGN PATENT DOCUMENTS

2249006  5/1975  France .

*Primary Examiner*—Frances Han
*Attorney, Agent, or Firm*—Roylance, Abrams, Berdo & Goodman

[57] ABSTRACT

An unloading facility for receiving a particulate material, such as coal, from a vehicle, and then conveying the particulate material to another location. The unloading facility primarily includes a platform assembly for supporting the vehicle, a bin for receiving the particulate material from the vehicle located beneath the top surface of the platform assembly, a bin door and bumper assembly for covering the open upper end of the bin to permit the vehicle to be driving over the bin and for preventing the vehicle from rolling backwards into the bin, a product sampling assembly, a product analyzer, and a conveying system with divider gates for transporting the particulate material from the bin to one of a plurality of stockpiles based on information obtained regarding the particular material. The platform assembly includes a scale for supporting and weighing the vehicle adjacent the forward and rearward ends of the bin so that the weight of the particulate material can be determined without moving the vehicle. The product sampling assembly includes a computer directed sampler, a sample crusher, a sample divider and a multi-can sample station with a motor coupled thereto. Preferably, the unloading facility is completely automatic, and also includes a control system having a card reader and computer for automatically controlling the conveying system, the bin door and bumper assembly, the product sampling assembly, the product analyzer and the diverter gates.

30 Claims, 6 Drawing Sheets

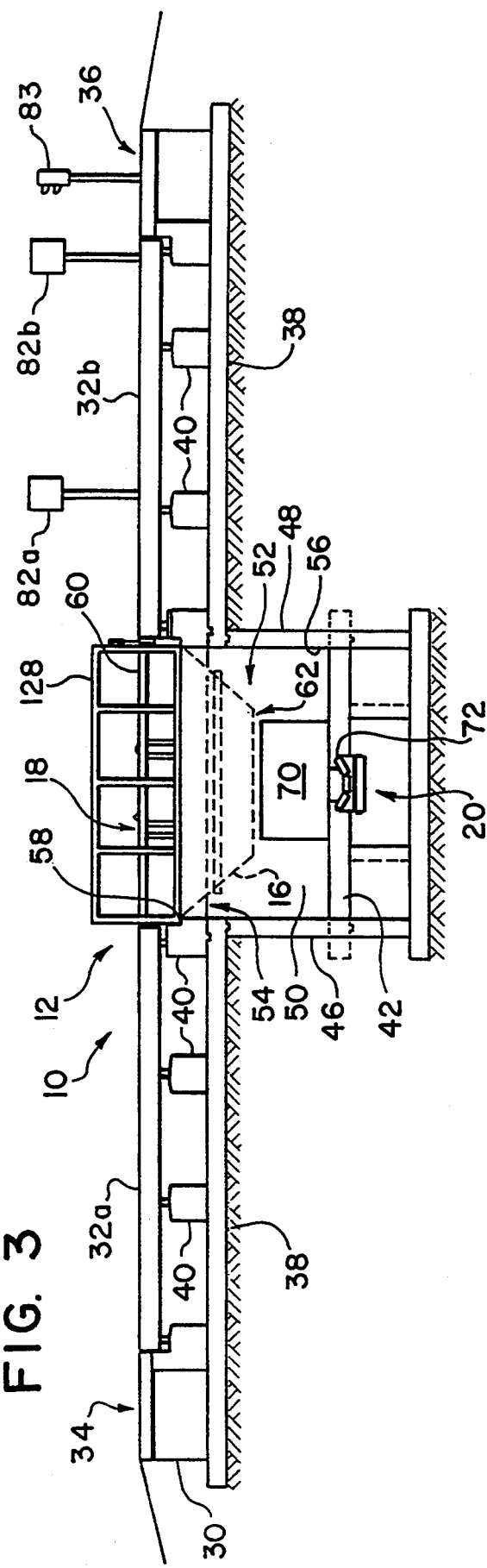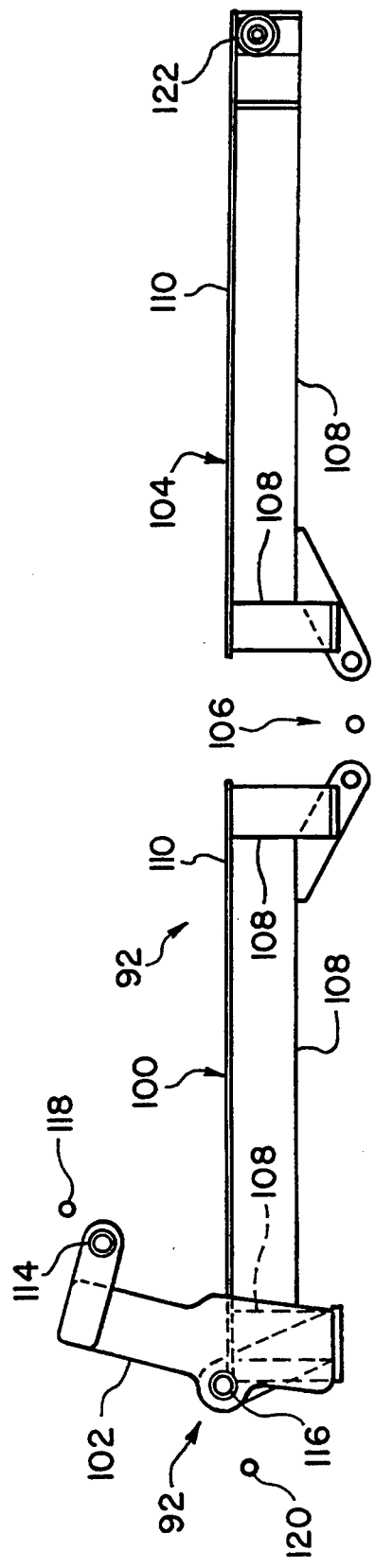

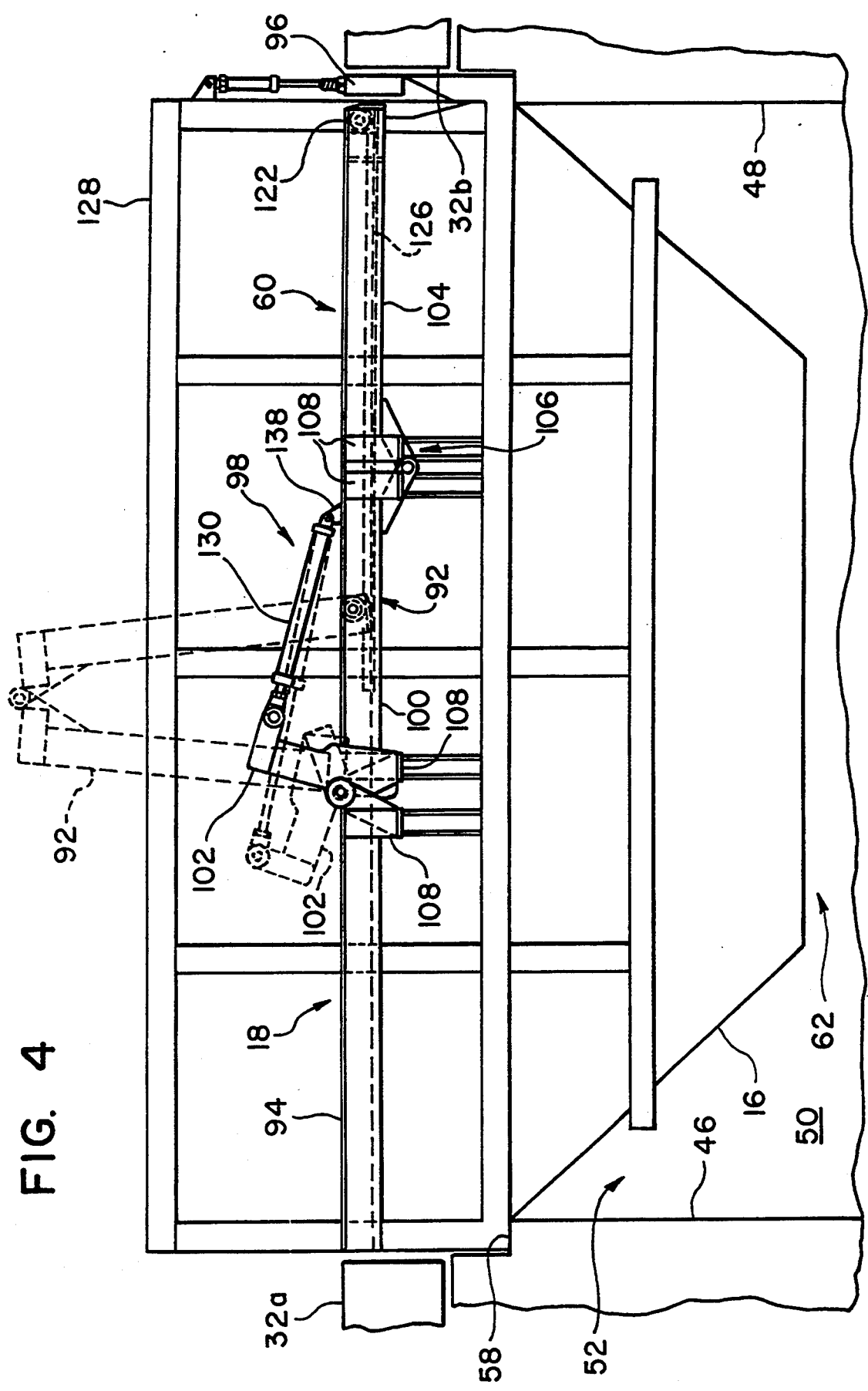

VEHICLE UNLOADING FACILITY WITH COMPUTER DIRECTED SAMPLING

This is a continuation of application Ser. No. 07/932,558 filed on Aug. 20, 1992, now abandoned, which is a continuation-in-part of Ser. No. 07/588,829, filed on Sep. 27, 1990, now abandoned of which the entire disclosure is hereby incorporated herein by reference.

FIELD OF THE INVENTION

This invention relates to systems or facilities for receiving material from a vehicle and transferring the material to another location. More specifically, this invention relates to automatic vehicle unloading facilities for receiving material from a dump truck, recording information regarding the material and transferring the material to one of a plurality of stockpiles based on the information obtained regarding the material. Also, this invention relates to sampling a portion of the load of material based on the weight of the load of material and transferring the sample portion to a sample can based on information obtained regarding the material.

BACKGROUND OF THE INVENTION

In the past, unloading and storage facilities for unloading, receiving and storing particulate materials, such as coal, required the dump truck or vehicle to be backed up to the storage bin or area for unloading the particulate material. Accordingly, this prior procedure of unloading particulate material from trucks is very time consuming and requires a large area for the trucks to maneuver, especially when very large trucks are using the facility. Moreover, there is some risk of injury or damage if a person or object is located or moves behind the truck, out of the driver's field of vision, when the truck is being backed up to the unloading bin.

Also, these prior storage facilities typically require several workers to be present to operate the storage facility. In particular, the workers of the storage facility have to process each vehicle including recording information about the origin of the load carried by the vehicle, weighing the load of particulate material and operating the storage facilities equipment for unloading particulate material from the vehicle or dump truck. Accordingly, the cost of operating such a storage facility can be very expensive.

Moreover, many of these prior unloading and storage facilities do not provide for segregation of different loads being dumped at the storage facilities. In other words, in many of these prior storage facilities loads of different qualities are often mixed together.

Examples of prior material handling facilities are disclosed in U.S. Pat. Nos. 396,197 to Dodge; 2,251,990 to Young; 3,606,050 to Silver; 3,802,584 to Sackett, Sr. et al; 4,358,238 to Ely; 4,669,674 to Oldengott et al; and 4,813,839 to Compton. Another material handling facility is disclosed in French Patent 2,249,006 to Frossard.

Examples of prior coal sampling and/or analyzing devices are disclosed in U.S. Pat. Nos. 4,314,241 to La Plante et al; 4,326,425 to Gundersen et al; 4,359,639 to Wykes et al; 4,370,201 to Lowenhaupt; 4,486,894 to Page et al; 4,531,093 to Rollwitz et al; 4,548,087 to Huck; 4,558,602 to Redding; 4,562,044 to Bohl; 4,582,992 to Atwell et al; 4,591,718 to Amer; 4,631,125 to Parks; 4,799,799 to Sapko et al; 4,841,153 to Wormald; 4,882,927 to Gould; and 4,916,719 to Kawatra et al, which are all hereby incorporated herein by reference.

In view of the above, it is apparent that there exists a need for a vehicle unloading facility, which is relatively fast, efficient, safe and economical to operate. This invention addresses this need in the art, along with other needs which will become apparent to those skilled in the art once given this disclosure.

While the description of this invention herein is directed at the unloading, receiving and transporting of particulate material, the facilities according to this invention could be designed to handle other materials, including liquids.

SUMMARY OF THE INVENTION

This invention provides a method of receiving materials from a vehicle, comprising the steps of supporting a vehicle filled with a load of material above and adjacent an upper end of a bin; unloading material from the vehicle into the bin through an opening in the upper end of the bin; transporting the material from the bin to another location; obtaining information regarding various aspects of the load of material; and diverting the material to one of a plurality of stock piles based on the information obtained regarding the material.

Another embodiment of this invention is provided by a method of receiving material from a vehicle, comprising the steps of weighing a vehicle filled with a load of material, supporting the vehicle filled with a load of material on a platform above and adjacent an upper end of a bin, unloading the material from the vehicle into the bin through an opening in the upper end of the bin, reweighing the vehicle after unloading the material from the vehicle into the bin to determine the weight of the load of the material, recording the weight of the load of the material unloaded into the bin for controlling the volume of material to be sampled, transporting the material from the bin to another location, and removing a sample portion of the material being transported from the bin with the volume of the sample portion being based upon the weight of the load of material from the vehicle.

In yet other embodiments of this invention, the vehicle unloading facility includes a control assembly utilizing a card reader and computer for automatically operating and controlling the bin door, the bumper, the conveying system, the sampling system and product analyzer.

The vehicle unloading facilities according to this invention have many advantages over prior vehicle unloading facilities presently employed for the same or similar purposes.

One advantage of the vehicle unloading facilities according to this invention is that the facilities are more efficient and economical than the prior vehicle unloading facilities.

Another advantage of the vehicle unloading facilities according to the present invention is that the facilities are safer since the vehicles do not have to be backed up to unload.

Another advantage of the vehicle unloading facilities according to the present invention is that operators do not have to be present to operate the facility.

A further advantage of the vehicle unloading facilities according to the present invention is that each load dumped into the bin is immediately carried away so that each load can be segregated and sampled at the time of dumping automatically.

Yet another advantage of the vehicle unloading facilities according to the present invention is that the facilities are capable of handling vehicles of various sizes.

Still another advantage of the vehicle unloading facilities of this invention is that vehicles can be unloaded relatively fast and the particulate material transported to a storage area containing similar particulate material.

A further advantage of the vehicle unloading facilities of this invention is that the weighing and unloading of the particulate material is accomplished at one location.

A further advantage is that the vehicle unloading facilities according to this invention can receive and handled materials of various sizes.

Yet another advantage of the vehicle unloading facilities according to this invention is that the drivers of the vehicles may remain at the vehicles at all times during the unloading process.

Yet another advantage of the vehicle unloading facilities according to this invention is that the operation may be fully automatic; thus completely eliminating human error.

Other advantages and salient features of the invention will become apparent from this disclosure. Certain embodiments of this invention will now be described with respect to the drawings which form part of this disclosure.

BRIEF DESCRIPTION OF THE DRAWINGS

FIG. 3 is a partial side elevational view of the vehicle unloading facility of FIGS. 1 and 2 with portions removed for clarity;

FIG. 4 is an enlarged, partial side elevational view of a bin door and bumper assembly rigidly coupled to a bin of the vehicle unloading facility of FIGS. 1-3;

FIG. 5 is an exploded side elevational view of a folding bin door in accordance with the present invention;

DETAILED DESCRIPTION OF THE INVENTION

Figure 1:
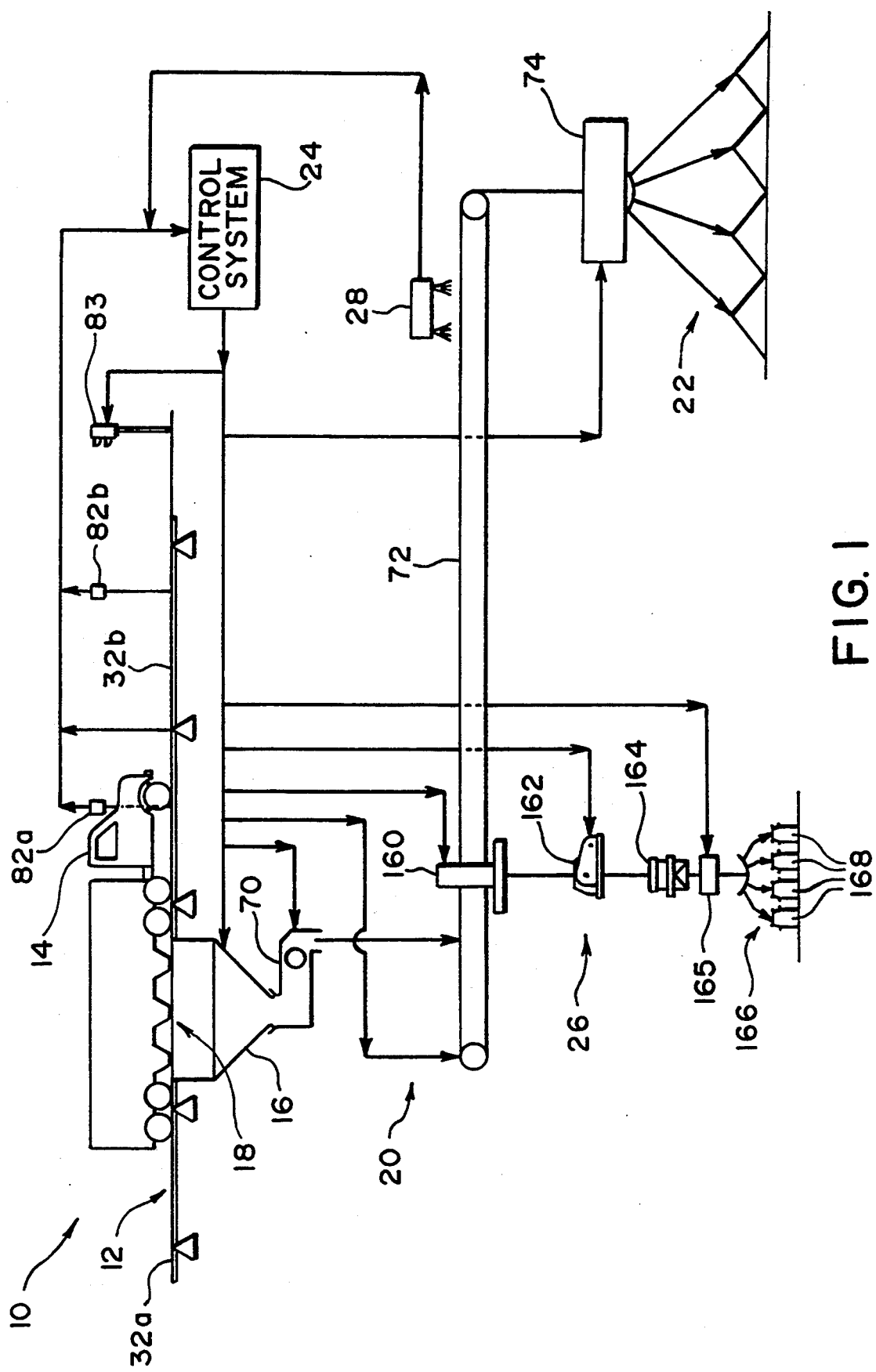
FIG. 1 is a schematic diagram of one embodiment of a vehicle unloading facility in accordance with the present invention and illustrating a bottom dump vehicle.

Referring to the Figures, and in particular FIG. 1, an unloading facility 10 according to this invention is illustrated, and primarily includes a platform assembly 12 for supporting a vehicle 14 filled with a load of particulate material, such as coal, gravel, sand, etc., a bin 16 for receiving the particulate material from vehicle 14 therein, a bin door and bumper assembly 18 for covering and uncovering bin 16, a conveying system 20 for transporting the particulate material from bin 16 to one of a plurality of storage piles or areas 22 and a control system 24 for automatically operating bin door and bumper assembly 18 and conveying system 20. The vehicle unloading facility 10 also includes a product sampling system 26 and a product analyzer 28, which are both automatically controlled by control system 24.

Figure 2:
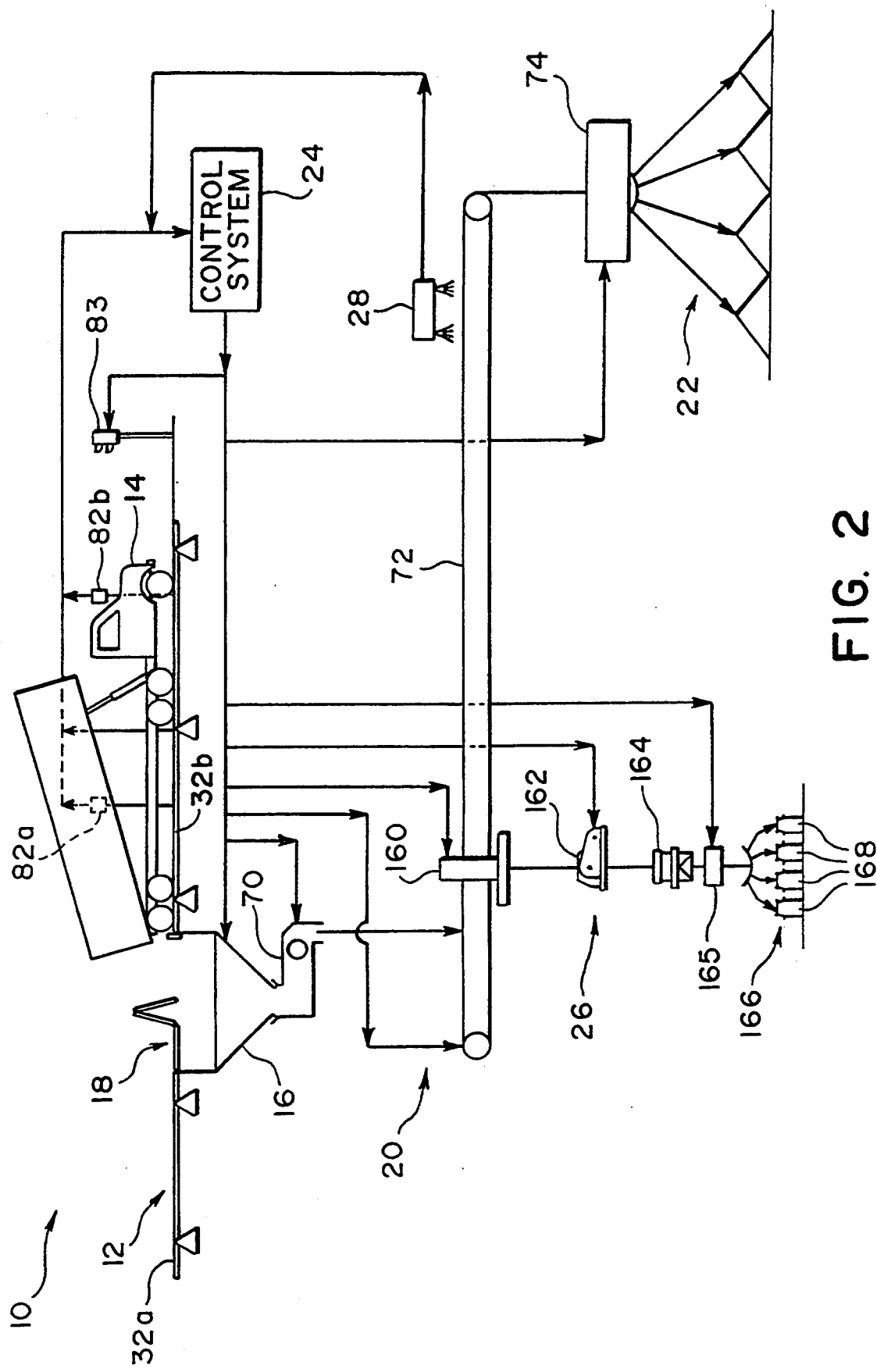
FIG. 2 is a schematic diagram of the vehicle unloading facility of FIG. 1 and illustrating a rear dump vehicle.
Figure 6:
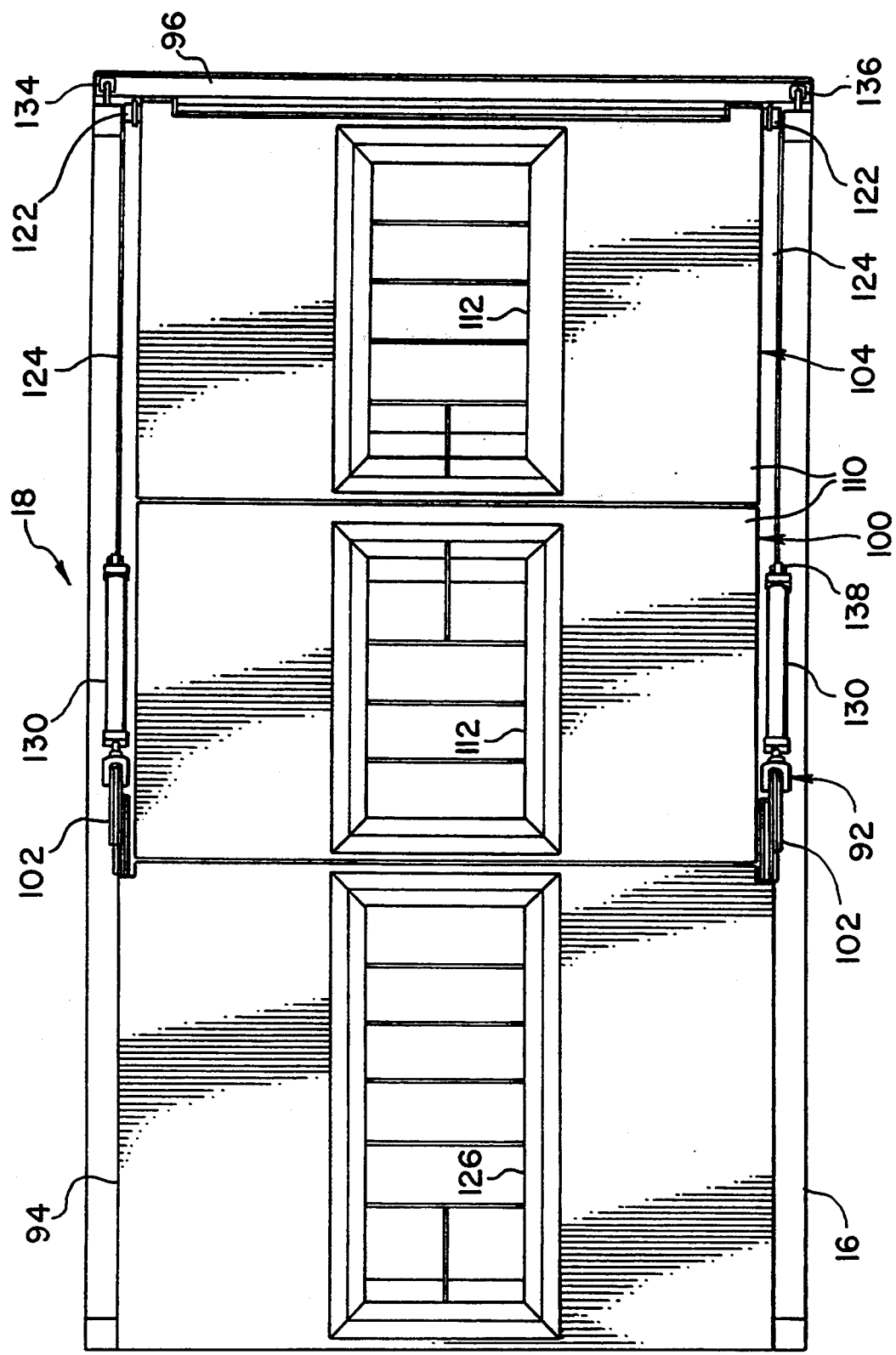
FIG. 6 is a top plan view of the bin door and bumper assembly of the present invention illustrated in FIGS. 1-4 with portions removed for clarity.

FIGS. 1 and 2 illustrate the vehicle unloading facility 10 being utilized to unload coal from vehicle 14 into bin 16 and then transporting the coal to one of the storage piles or areas 22. Of course, vehicle unloading facility 10 is not limited to this use. Vehicle unloading facility 10 can be employed to unload vehicles filled with other particulate material such as gravel, sand, etc.

Basically, in operation, vehicle 14 approaches vehicle unloading facility 10 from the left, as shown in FIGS. 1 and 2, drives over bin door and bumper assembly 18 and parks either over bin door and bumper assembly 18 as seen in FIG. 1 or adjacent to the right or forward end of bin door and bumper assembly 18 as seen in FIG. 2.

In FIG. 1, the chutes of vehicle 14 are aligned with openings in the bin door and bumper assembly 18 as discussed below. The driver of vehicle 14 then activates control system 24 which in turn activates the facility 10. Next, the driver dumps or unloads the particulate material from vehicle 14 into bin 16 in a conventional manner. The particulate material is then transported from bin 16 by conveying system 20 to one of the storage piles or areas 22 and sampled by sampling system 26 as discussed in more detail below.

In FIG. 2, the rear end of vehicle 14 is adjacent to or overlaps the forward end of bin 16. The driver of vehicle 14 then activates control system 24 which in turn activates bin door and bumper assembly 18 so that the doors open to expose the open upper end of bin 16. Next, the driver dumps or unloads the particulate material from vehicle 14 into bin 16 in a conventional manner. The particulate material is then transported from bin 16 by conveying system 20 to one of the storage areas 22 as discussed in more detail below.

Referring to FIG. 3, platform assembly 12 includes a concrete support member 30 partially buried beneath the earth, and a pair of vehicle or truck scale 32a and 32b supported on concrete support member 30. Truck scales such as truck scale 32a and 32b are well known in the art, and thus truck scales 32a and 32b are not illustrated or described in detail herein. Examples of truck scales that can be used with this invention are scales manufactured by Unibridge Corporation.

As seen in FIG. 1, the bottom dump vehicle 14 straddles bin door and bumper assembly 18 so that the rear tires of vehicle 14 rests upon scale 32a and the front tires rests upon scale 32b. The weight of the load of particulate material is then determined by subtracting the weight of vehicle 14 from the total weight of the vehicle 14 plus the load of particulate material. The weight of load is accomplished without moving vehicle 14 since the weight of vehicle 14 with the load therein is recorded by a computer in control system 24. Likewise, after dumping the load of particulate material the weight of the vehicle without the load of particulate material is immediately recorded by the computer in control system 24 so that the weight of the load of particulate material can be calculated.

Referring now to FIG. 2, the rear dump vehicle 14 rests completely on scale 32b so that the weight of the load of a rear dump vehicle can be determined in substantially the same manner as described above for a bottom dump vehicle.

Concrete support member 30 has a first or rearward end 34 and a second or forward end 36 with its longitudinal axis extending therebetween, and includes a base portion 38, and a plurality of concrete pillars 40 extending upward from base portion 38 for supporting truck scales 32a and 32b with their upper surfaces substantially flush with the upper surface of bin door and bumper assembly 18. The concrete support member 30 also includes a bottom wall 42 and three planar side walls 46, 48 and 50 extending upwardly from a bottom wall 42 to form a bin cavity 52 which receives and suspends bin 16 and a portion of conveying system 20 therein.

As seen in FIG. 3, bin cavity 52 is formed by the three planar side walls 46, 48 and 50 extending vertically upwardly from bottom wall 42 and has open upper end 54 and open side 56. Side walls 46, 48 and 50 form a three-sided support edge 58 along their top edges for supporting the bin door and bumper assembly 18 and bin 16 as discussed below.

Referring now to FIGS. 3 and 4, bin 16 is received in bin cavity 52, and includes four steel trapezoidal shaped sides rigidly coupled together on edge to form a funnel with a rectangular open upper end 60 for receiving the particulate matter therein and a smaller rectangular open lower end or discharge opening 62 for directing the particulate material downwardly to a portion of conveying system 20. Bins such as bin 16 are well known in the art, and thus bin 16 is not illustrated or described in detail herein.

Conveying system 20 includes a coal feeder and breaker 70 for receiving the particulate material or coal from bin 16, a first conveyor 72 for transporting the particulate material from coal feeder and breaker 70 and a plurality of diverter gates 74 for transporting the particulate material from first conveyor 72 to one of the plurality of storage areas 22. While only first conveyor 72 is illustrated for conveying material between breaker 70 and diverter gates 74, it will be apparent to those skilled in the art that several conveyors can be utilized.

Coal feeder and breakers such as coal feeder and breaker 70 are well known in the industry, and thus will not be discussed or illustrated in detail herein. An example of coal feeder and breakers which could be used with this invention are manufactured by the Stamler Corporation.

Preferably, coal feeder and breaker 70 is supported below bin 16 for receiving and transporting the particulate material from bin 16 to first conveyor 72 as shown in FIGS. 1 and 2. Coal feeder and breaker 70 can be fixedly coupled below bin 16 in any conventional manner.

It should be apparent to those skilled in the art that if vehicle unloading facility 10 is not being utilized to handle coal or if coal feeder and breaker 70 is not needed, then coal feeder and breaker 70 can be substituted with a conveyor or other convention devices which will transport the particulate material from bin 16 to first conveyor 72.

First conveyor 72 is preferably a conventional endless belt conveyor for transporting the particulate material from coal breaker 70 or bin 16 to diverter gates 74. Since endless belt conveyors such as conveyor 72 are well known in the industry, conveyor 72 will not be discussed or illustrated in detail herein.

Computer directed diverter gates 74 are electrically coupled to computer 84 of control system 24 for directing and segregating the load of particulate material to one of the plurality of stock piles 22 based on the information obtained either from card reader 82a or 82b, or from product analyzer 28. Accordingly, diverter gates 74 segregate the material to one of a plurality of stock piles 22 such that all particulate material is directed to a stock pile having similar qualities.

Diverter such as diverter gates 74 are well known in the art, and thus will not be discussed or illustrated in detail herein. Preferably, diverter gates 74 are manufactured by Coal Systems Corporation.

Figure 7:
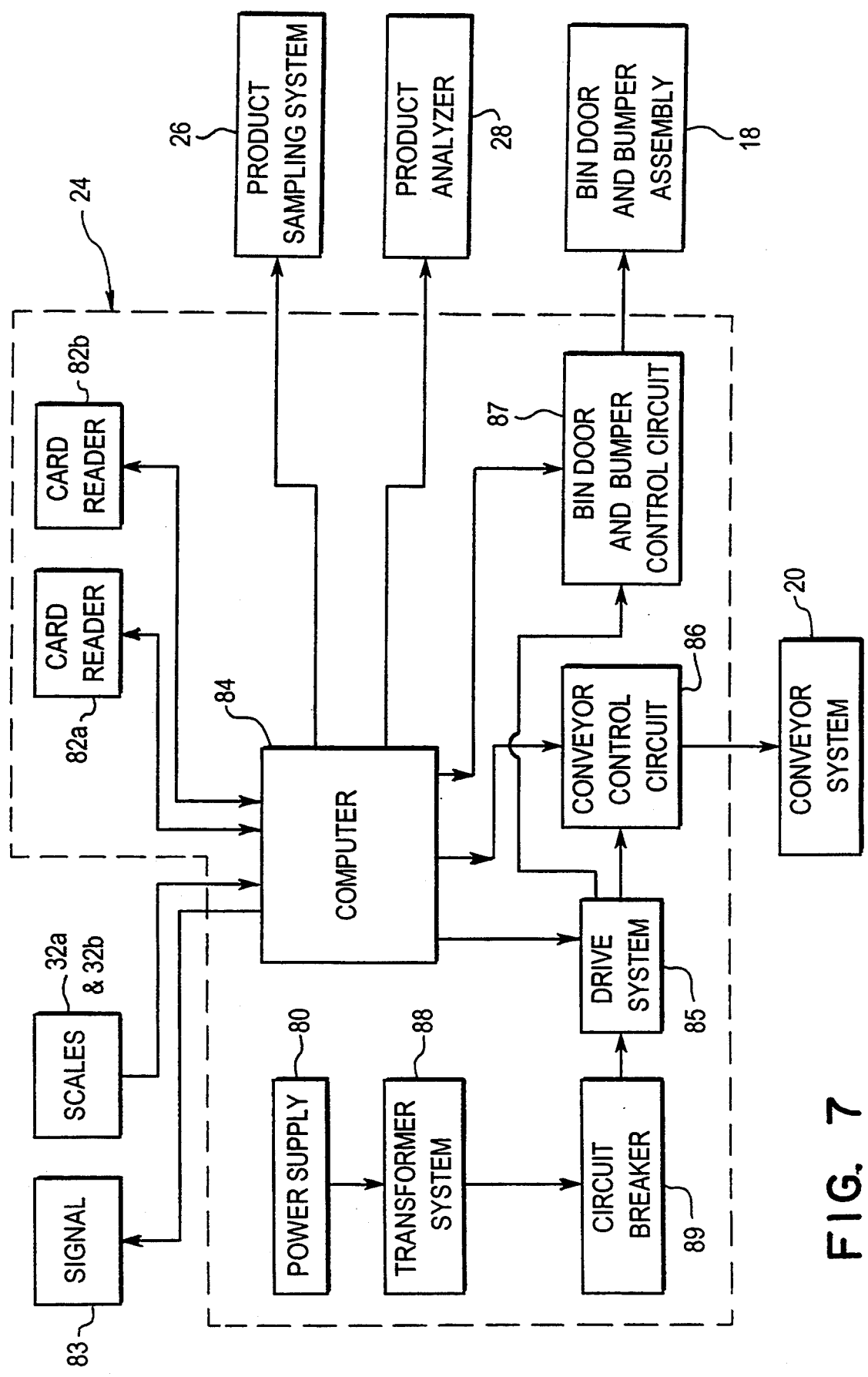
FIG. 7 is a schematic diagram of a control system utilized to operate the embodiment illustrated in FIGS. 1-6.

Referring now to FIG. 7, control system 24 is schematically illustrated, and includes a power supply 80, a pair of card readers 82a and 82b, a computer 84, a drive system 85, a conveyor control circuit 86, a bin door and bumper control circuit 87, a transformer system 88 and a circuit breaker 89, which are all electrically coupled together in a conventional manner.

The power supply 80 is preferably a three phase electrical motor which is electrically coupled to conventional drive system 85 via conventional transformer system 88 and conventional 600 amp main circuit breaker 89. Power supplies, transformer systems and main circuit breakers are well known in the industry, and thus will not be discussed or illustrated in detail.

Card readers 82a and 82b are preferably card readers such as those manufactured by Compro Systems, Inc. Card readers 82a and 82b are activated by a control card carried by the vehicle's driver. The driver inserts the control card into either card reader 82a or 82b to operate vehicle unloading facility 10. For convenience a pair of card readers 82a and 82b are located adjacent scale 32b (see FIGS. 1 and 2) so that either card reader 82a or 82b is readily accessible to drivers of either bottom dump or rear dump vehicles unloading at facility 10. In fact, card readers 82a and 82b can be located such that they are accessible from the cabs of such vehicles so that the drivers do not have to leave their vehicle cabs to unload at facility 10.

The control card contains various information about the particulate material being dumped, i.e., origin of the particulate material, etc. Upon insertion of the control card into one of the card readers 82a and 82b, the computer 84 reads and records this information, and then activates motors and hydraulic units as necessary to open bin door 92, extend bumper 96, start coal breaker and feeder 70, and start conveyor 72 product sampling system 26 and product analyzer 28, as discussed above.

Card readers and computers such as card readers 82a and 82b and computer 84 are well known in the industry, and thus will not be discussed or illustrated in detail herein.

Likewise, the software and hardware utilized with computer 84 are readily prepared by qualified programmers to meet the needs of any given facility.

A conveyor control circuit 86 controls the operation of conveyor system 20, and especially diverter gates 74 for directing the particulate material to a storage area or silo 22. Conveyor control circuits such as conveyor control circuit 86 are well known in the industry, and thus will not be discussed in detail herein.

Bin door and bumper control circuit 87 controls the operation of bin door and bumper assembly 18 and is activated by inserting a control card into one of the card readers 82a or 82b (described below). Bin door and bumper control circuit 87 is provided with a timer circuit to shut down the unloading facility 10 after a predetermined time (i.e., to close the bin door, retract the bumper 96 and shut off coal breaker 70, conveyor 72, product sampling system 26 and product analyzer 28).

Since circuits such as bin door and bumper control circuit 87 and timer circuits are known in the industry, they will not be discussed or illustrated in detail.

Preferably upon initially inserting a control card into either card reader 82a or 82b, the bin door and bumper control circuit 87 will open folding bin door 92 and extend bumper 96 upwardly, if necessary, and start coal feeder and breaker 70, conveyor 72, product sampling system 26 and product analyzer 28.

After the particulate material is unloaded into bin 16, the control card is reinserted into one of the card readers 82a or 82b to close bin door 92 and retract bumper 96 if necessary. Card reader 82a or 82b will then, dispense a ticket indicating the weight of the particulate material dumped into bin 16, and will activate the timer circuit to shut down coal feeder and breaker 70 and conveyor 72 after a predetermined time, such as thirty minutes, if a control card is not inserted within the predetermined period of time. Also, bin door and bumper control circuit 87 operates a signal 83 to turn on a red light when the bin door 92 is open to warn vehicles approaching the unloading facility 10, and a green light when the bin door 92 is closed. Signal light 83 is mounted in any suitable location, which is visible to the approaching vehicles.

As seen in FIG. 4 and 5, bin door and bumper assembly 18 includes a folding bin door 92, a rectangular, metal check plate assembly 94, a bumper 96, and a hydraulic system 98. Bin door and bumper assembly 18 is rigidly coupled to the upper end of bin 16 which rests upon support edge 58 of concrete support member 30 such that bin door and bumper assembly 18 overlies bin cavity 52.

When bin door 92 is in the down or closed position, the upper surface of bin door and bumper assembly 18 forms a substantially continuous surface with the upper surfaces of concrete support member 30 and truck scales 32a and 32b. Accordingly, bin door and bumper assembly 18 permits vehicles to drive over bin 16 and park either over or at the forward end of bin 16 so as to be ready to dump the particulate material into bin 16 without backing up.

Folding bin door 92 includes a first door section 100 pivotally coupled at one end to the upper edge of bin 16 by a pair of crank arms 102 and a second door section 104 pivotally coupled to the other end of first door section 100 by a hinge 106. Specifically, door sections 100 and 104 pivot about horizontal axes oriented substantially perpendicular to the longitudinal axis of platform assembly 12 and bin door and bumper assembly 18.

Door sections 100 and 104 are preferably formed in a conventional manner such as by a plurality of tubular support members 108 rigidly coupled together with a rectangular steel check plate 110 overlying and rigidly coupled to support members 108 to form two rectangular doors. Each check plate 110 is provided with a central rectangular opening 112 for receiving particulate material therethrough and into bin 16.

Crank arms 102 are substantially L-shaped and rigidly coupled to two adjacent corners of door section 100. Each crank arm 102 has a pair of pivot holes 114 and 116 for receiving pivot pins 118 and 120, respectively.

Door section 104 includes a pair of rollers 122 rotatably coupled to the corners opposite of hinge 106. Rollers 122 are supported on bin 16 by a pair of guide rails 124 which are rigidly fixed to bin 16. Upon opening folding bin door 92, door section 100 will swing upwardly pulling door section 104 rearwardly and upwardly therewith while the free end of door section 104 slides along rails 124 by rollers 122.

Check plate assembly 94 is rigidly coupled to the upper end of bin 16, and includes a rectangular opening 126 for receiving particulate matter therethrough and then into bin 16. Check plate assembly 94 together with check plates 110 form a substantially flat horizontal surface for permitting vehicle 14 to drive over bin 16.

Bumper 96 is oriented for vertical movement from a retracted position beneath the horizontal plane of check plate 110 to an extended position above the horizontal plane of check plate 110. Bumper 96 is moved between the retracted and extended position by hydraulic system 98 as discussed below.

Hydraulic system 98 includes a pair of hydraulic cylinders 130 pivotally coupled to crank arms 102 and the sides of bin 16 for pivoting door sections 100 and 104 between open and close positions, and a pair of hydraulic cylinders 134 coupled to the ends of bumper 96 and to the ends of the side rails 128 for moving bumper 96 between its retracted and extended positions.

Since hydraulic systems such as hydraulic system 98 are well known in the art, the hydraulics of hydraulic system 98 will not be discussed or illustrated in detail herein.

Hydraulic cylinders 130 are rotatably coupled at one end in pivot holes 114 of crank arms 102 and at the other end to a pair of flanges 138 mounted on bin 16. When hydraulic cylinders 130 and 132 are extended, assuming door sections 100 and 104 are in the closed positions, hydraulic cylinders 130 will rotate crank arms 102. Since crank arms 102 are fixedly attached to door section 100 and rotatably coupled to bin 16, rotation of crank arms 102 about their horizontal axes causes door sections 100 and 104 to pivot upwardly.

To return door sections 100 and 102 to the down or closed position, hydraulic cylinders 130 and 132 are retracted, causing crank arms 102 to rotate in the opposite direction until 100 and 104 rests on gusset or support plates (not shown).

Product sampling system 26 includes a computer directed hammer sampler 160 positioned adjacent conveyor 72, a sample crusher 162 positioned adjacent hammer sampler 160, a sample divider 164 positioned to receive the crushed sample from sample of material crusher 162, a multi-can sample station 166 for receiving the crushed sample of material in one of a plurality of sample cans 168, and a motor 165 operatively coupled between sample divider 164 and multi-can sample station 166 for indexing sample cans 168.

Computer directed hammer sampler 160 is preferably a sweep arm type sampler, such as the sweep arm samplers manufactured by Sieb Technique or Tema Systems. Since hammer or sweep arm samplers such as sampler 160 are well known in the industry, sampler 160 will not be discussed or illustrated in detail herein.

Hammer sampler 160 is controlled by computer 84 of control system 24 to remove the required quantity of material as required by regulation, i.e., ASTM regulations. In particular, sampler 160 removes or samples a volume of material based upon the weight of the load of particulate material dumped from vehicle 14. In other words, the amount of the sample portion removed from each load of material dumped at unloading facility 10 depends on the weight of the load of material dumped by the vehicle 14.

The weight of each load of material is calculated by computer 84 via scales 32a and 32b. Specifically, computer 84 records the weight of vehicle 14 filled with a load of material, and then records the weight of the vehicle after unloading the material from the vehicle in the bin to calculate the weight of the load of the material. Computer 84 then directs sampler 160 to remove the necessary volume of material for testing.

The sample portion of each load of particulate material is then conveyed from sampler 160 to sample crusher 162 for breaking the particulate material into smaller particles suitable for testing.

Sampler crusher 162 is preferably a crusher such as the crushers manufactured by Tema Systems. Since crushers are well known in the industry, crusher 162 will not be discussed or illustrated in detail herein.

Sample divider 164 receives the crushed sample portion of the particulate material from sample crusher 162 and directs the crushed sample portion to a sample can 168 at multi-can sample station 166. Motor 165 is electrically coupled to computer 84 of control system 24 for indexing sample cans 168 so that the sample portion is directed to the correct sample can 168. Computer 84 determines which sample can 168 receives the sample portion of the material. Specifically, the driver of the vehicle 14 has a control card which is inserted into either control reader 82a or 82b for providing information on various aspects of the load of material to computer 84 of control system 24. Computer 84 then records this information and then indexes sample cans 168 by motor 165 for directing the sample portion to the appropriate sample can 168.

Sample divider 164 is preferably a divider such as the dividers manufactured by Tema Systems. Since dividers and motors are well known in the industry, sample divider 164 and motor 165 are not be discussed or illustrated in detail herein.

Multi-can sample station 166 is preferably a multi-can sample station as those manufactured by Tema Systems. Since multi-can sample stations are well known in the industry, multi-can sample station 166 will not be discussed or illustrated in detail herein.

For example, the control card contains information on the origin of the particulate material, i.e., mine or facility, such that control system 20 indexes sample cans 168 by motor 165 to deposit the sample portion of pre-crushed material into a sample can 168 marked for that mine. Alternatively, the sample portion of crushed material can be sorted into cans 168 depending upon other information, if desired.

The sample cans 168 are then taken to a testing laboratory for conducting detailed analysis on the sample particulate material to determine its precise composition. This information can then be used to store calibration curves on various product qualities from a particular mine in computer 84 of control system 24 for fine tuning the product analyzer 28. In other words, a sample portion of material from a particular mine is tested to determine the material's composition and other properties. This information on the material is then stored in computer 84. When a control card is inserted into one of the card readers 82a or 82b, the computer 84 will read the control card to determine the origin of the material and send the calibration curves to product analyzer 28 for that particular mine. This insures the accuracy of product analyzer 28.

Product analyzer 28 is electrically coupled to computer 84 of control system 24 for analyzing the load of particulate matter as it passes along conveyor 72. Product analyzer 28 measures various aspects of the load of material such as moisture content, ash content, iron content, sulfur content, etc. The product analyzer 28 then conveys this information on the particulate material to computer 84 which records this information and sends a signal to the computer directed diverter gates 74 so that the particulate material is directed to one of the stock piles 22 having similar characteristics or quality. Preferably, product analyzer 28 is a product analyzer such as those manufactured by Coal Scan.

Product analyzers such as product analyzer 28 are well known in the art, and thus will not be discussed or illustrated in detail herein.

Operation

In operation, vehicle unloading system 10 is designed so that vehicles, such as vehicle 14, can unload their load of particulate material in a relatively fast, efficient and safe manner without the need for any operators to be present at the vehicle unloading facility 10.

In particular, vehicle 14 drives onto the rearward end of platform assembly 12, i.e., from left to right as viewed in FIGS. 1–3, over the bin door and bumper assembly 18 and then parks on either truck scale 32a or on both truck scales 32a and 32b. In a bottom dump vehicle, the vehicle 14 straddles bin door and bumper assembly 18 such that the vehicle rests on both scales 32a and 32b. In a rear dump vehicle, the rear end of the vehicle is immediately adjacent or overlapping the forward end of bin door and bumper assembly 18. The driver then inserts a control card containing various information on the particulate material into the appropriate card reader 82a and 82b to activate the computer 84 which in turn activates drive system 85 and circuits 86 and 87 to operate bin door and bumper assembly 18, conveying system 20, product sampling system 26 and product analyzer 28. Computer 84 also stores the information contained on the control card and records the gross weight of the vehicle with the load of material.

More specifically, upon insertion of a control card into card reader 82a or 82b, the computer 84 will determine if the vehicle is a rear dump vehicle or a bottom dump vehicle. If vehicle 14 is a rear dump vehicle, then computer 84 will energize bin and bumper control circuit 87 to retract bin door 92 (as discussed above), while simultaneously extending bumper 96 upwardly to prevent the rear dump vehicle from rolling back into the open upper end 60 of bin 16. If the vehicle is a bottom dump vehicle, then the computer 84 will not energize bin and bumper control circuit 87.

Next, the driver dumps the load of particulate material into bin 16 where it is funnelled to coal breaker 70 or some other conveying device. The coal breaker 70 will break the coal up to a manageable size and transport it to the lower end of first conveyor 72 which will then in turn convey the coal to diverter gates 74 for delivery to the appropriate stockpile 22. As mentioned above, computer 84 controls diverter gates 74 to direct the material to the appropriate stock 22 either based on the quality of the material as determined by product analyzer 28 or based on information from the control card such as vehicle origination.

Also, automatically and simultaneously the sampling system 26 removes a portion of the load for testing.

Before and after vehicle 14 is unloaded, scale 32 will weigh the vehicle and convey the weight to computer 84 so that the weight of the load dumped into bin 16 can be determined and recorded.

The driver then, reinserts the control card into the appropriate card reader 82a or 82b to obtain a ticket indicating the weight of the load dumped into bin 16. This also causes bin door and bumper control circuit 87 to close bin door 92, to retract bumper 96 and to shut down coal feeder and breaker 70, conveyor 72 and product sampling system 26 after a predetermined time if another control card is not inserted within the predetermined period of time.

Various modifications, improvements and other embodiments will become apparent to those skilled in the art once given this disclosure. Such modifications, improvements and other embodiments are considered to be within the scope of this invention as defined by the following claims.

What is claimed is:

1. A method of receiving coal from a vehicle, comprising the steps of
supporting a vehicle filled with a load of coal above and adjacent an upper end of a bin,
unloading the load of coal from the vehicle into the bin through an opening in the upper end of the bin,
transporting substantially the entire load of coal from the bin to another location,
obtaining information regarding various aspects representative of substantially the entire load of coal,
sending the information regarding various aspects representative of substantially the entire load of coal to a control means, and
diverting substantially the entire load of coal to one of a plurality of stock piles based on the information obtained regarding the load of coal by using diverting means operated by the control means for diverting the load of coal.

2. A method according to claim 1, wherein the step of obtaining information includes the step of
analyzing the load of coal being transported to determine various properties of the load of coal for determining which one of the plurality of stock piles will receive the load of coal.

3. A method according to claim 2, wherein the step of analyzing includes the step of
determining the amount of moisture in the load of coal.

4. A method according to claim 2, wherein the step of analyzing includes the step of
determining the amount of ash in the load of coal.

5. A method according to claim 2, wherein the step of analyzing includes the step of
determining the amount of iron in the load of coal.

6. A method according to claim 2, further comprising the steps of
weighing the vehicle filled with the load of coal and reweighing the vehicle after unloading the load of coal to determine the weight of the load of coal, and
removing a sample portion of the load of coal with the amount of the sample portion being removed based upon the weight of the load of coal.

7. A method according to claim 6, further comprising the step of
crushing the sample portion of coal into smaller pieces.

8. A method according to claim 7, further comprising the step of
inserting a control card bearing information on the load of coal contained in the vehicle into the control means to activate the control means and to record information on the coal.

9. A method according to claim 8, further comprising the step of
indexing crushed sample portion to one of a plurality of sample containers based upon the recorded information from the control card.

10. A method of receiving coal from a vehicle, comprising the steps of
supporting a vehicle filled with a load of coal above and adjacent an upper end of a bin,
unloading the load of coal from the vehicle into the bin through an opening in the upper end of the bin,
transporting substantially the entire load of coal from the bin to another location,
obtaining information regarding various aspects representative of substantially the entire load of coal,
diverting substantially the entire load of coal to one of a plurality of stock piles based on the information obtained regarding the load of coal,
weighing the vehicle filled with the load of coal and reweighing the vehicle after being unloaded to determine the weight of the load of coal; and
removing a sample portion of the load of coal with the amount of the sample portion removed being based upon the weight of the load of coal from the vehicle.

11. A method of receiving coal from a vehicle, comprising the steps of
supporting a vehicle filled with a load of coal above and adjacent an upper end of a bin,
unloading the load of coal from the vehicle into the bin through an opening in the upper end of the bin,
transporting substantially the entire load of coal from the bin to another location,
obtaining information regarding various aspects representative of substantially the entire load of coal,
diverting substantially the entire load of coal to one of a plurality of stock piles based on the information obtained regarding the load of coal, and
inserting a control card bearing information on the load of coal contained in the vehicle into a control means to activate the control means to obtain the information on the entire load of coal for directing substantially the entire load of coal to one of the plurality of stock piles.

12. A method of receiving coal from a vehicle, comprising the steps of
weighing a vehicle filled with a load of coal,
supporting the vehicle filled with a load of coal on a platform above and adjacent an upper end of a bin,
unloading the load of coal from the vehicle into the bin through an opening in the upper end of the bin,
reweighing the vehicle after unloading the load of coal from the vehicle into the bin to determine the weight of the load of coal,
recording the weight of the load of coal unloaded into the bin for controlling the volume of coal to be sampled,
transporting the load of coal from the bin to another location, and
removing a sample portion of the load of coal being transported from the bin with the volume of the sample portion removed being based upon the weight of the load of coal from the vehicle.

13. A method according to claim 12, further comprising the step of
crushing the sample portion of coal into smaller pieces.

14. A method according to claim 13, further comprising the step of
inserting a control card bearing information on the load of coal contained in the vehicle into a control means to activate the control means and to record information on the coal.

15. A method according to claim 14, further comprising the step of
indexing crushed sample portion to one of a plurality of sample containers based upon the recorded information from the control card.

16. A method according to claim 15, further comprising the steps of
obtaining information regarding various aspects of the load of coal, and
diverting the coal to one of a plurality of stock piles based on the information obtained regarding the coal.

17. A method according to claim 16, wherein the step of obtaining information includes the step of
analyzing the coal being transported to determine various properties of the coal for determining which one of the plurality of stock piles will receive the load of coal.

18. A method according to claim 16, wherein the step of obtaining information includes the step of
reading additional information from the control card regarding the load of coal in the vehicle to determine which one of the plurality of stock piles will receive the load of coal.

19. A coal unloading facility, comprising:
platform means for supporting thereon a vehicle filled with a load of coal, said platform means having a top surface, and first and second ends with a longitudinal axis extending therebetween;
a bin located substantially below the top surface of said platform means and having a forward end, a rearward end, an open upper end for receiving the load of coal from a vehicle located on said platform means and a discharge opening for removing the material from said bin;
conveying means for transporting substantially the entire load of coal from said bin, said conveying means being positioned to receive the material from said discharge opening;
diverting means for transporting and dumping substantially the entire load of coal from said conveying means to one of a plurality of stockpiles, said diverting means being positioned to receive substantially the entire load of coal from said conveying means; and
control means, operatively coupled to said diverting means, for automatically operating said diverting means to direct said diverting means to dump substantially the entire load of coal to one of a plurality of stockpiles based on information inputted in said control means regarding the coal, said control means including input means for receiving information on the coal to direct said diverting means to dump substantially the entire load of coal to one of said stockpiles based on said information inputted in said control means.

20. The coal unloading facility according to claim 19, further comprising
analyzing means for determining various properties of the load of coal being transported by said conveying means from said bin, and said control means being operatively coupled to said analyzing means and said diverting means to direct the coal to one of the plurality of stockpiled based on the properties of the coal.

21. The coal unloading facility according to claim 20, further comprising
sampling means for removing from the load of coal a predetermined sample portion of the coal unloaded into said bin for testing.

22. The coal unloading facility according to claim 21, further comprising
weighing means for weighing the vehicle filled with the load of coal and the vehicle after unloading the load of coal.

23. The coal unloading facility according to claim 22, wherein
said control means is operatively coupled to said sampling means and said weighing means to control the volume of the sample portion of coal.

24. A coal unloading facility, comprising:
platform means for supporting thereon a vehicle filled with a load of coal, said platform means having a top surface, and first and second ends with a longitudinal axis extending therebetween;
a bin located substantially below the top surface of said platform means and having a forward end, a rearward end, an open upper end for receiving the load of coal from a vehicle located on said platform means and a discharge opening for removing the coal from said bin;
conveying means for transporting substantially the entire load of coal from said bin, said conveying means being positioned to receive substantially the entire load of coal from said discharge opening;
diverting means for transporting and dumping substantially the entire load of coal from said conveying means to one of a plurality of stockpiles, said diverting means being positioned to receive substantially the entire load of coal from said conveying means; and
control means for automatically operating said diverting means to direct said diverting means to dump substantially the entire load of coal to one of a plurality of stockpiles based on information inputted in said control means regarding the coal,
said control means including a card reader for receiving and reading a control card bearing information regarding the load of coal being unloaded and to activate said control means and for providing information representative of substantially the entire load of coal to direct the diverting means.

25. The coal unloading facility according to claim 24, further comprising
sampling means for removing from the load of coal a predetermined sample portion of coal unloaded into said bin for testing.

26. The coal unloading facility according to claim 25, further comprising
weighing means for weighing the vehicle filled with the load of coal and the vehicle after unloading the load of coal.

27. The coal unloading facility according to claim 26, wherein
said control means is operatively coupled to said sampling means and said weighing means to control the volume of the sample portion of coal.

28. A coal unloading facility, the combination comprising:
platform means for supporting thereon a vehicle filled with a load of coal, said platform means having a top surface, and weighing means for weighing the vehicle filled with the load of coal and for weighing the vehicle after unloading the load of coal;

a bin located substantially below the top surface of said platform means and having a forward end, a rearward end, an open upper end for receiving the load of coal from a vehicle located on said platform means and a discharge opening for removing the load of coal from said bin;

conveying means for transporting substantially the entire load of coal from said bin, said conveying means being positioned to receive the load of coal from said discharge opening;

sampling means for removing from said conveying means a predetermined sample portion of each load of coal unloaded into said bin for testing to obtain information representative of the entire load of coal; and control means for controlling the volume of material removed from the load of coal based on the weight of the load of the coal unloaded into said bin, said control means being operatively coupled to said weighing means and said sampling means.

29. The coal unloading facility according to claim 28, further comprising a crushing means for crushing the sample portion, and said crushing means being positioned adjacent said sample means to receive the sample portion therefrom.

30. The coal unloading facility according to claim 29, further comprising indexing means for directing the sample portion to one of a plurality of sample cans, and said index means being operatively coupled to said control means.

* * * * *